United States Patent [19]

Guss et al.

[11] Patent Number: 4,565,695
[45] Date of Patent: Jan. 21, 1986

[54] SYNTHETIC PHEROMONE 10-METHYL-2-TRIDECANONE AND ITS USE IN CONTROLLING THE SOUTHERN CORN ROOTWORM AND RELATED DIABROTICITES

[75] Inventors: Paul L. Guss, Brookings, S. Dak.; James H. Tumlinson, III, Gainesville, Fla.; Philip E. Sonnet, Gainesville, Fla.; John R. McLaughlin, Gainesville, Fla.

[73] Assignee: The United States of America as represented by the Secretary of Agriculture, Washington, D.C.

[21] Appl. No.: 625,265

[22] Filed: Jun. 27, 1984

Related U.S. Application Data

[62] Division of Ser. No. 461,299, Jan. 27, 1983, Pat. No. 4,474,991.

[51] Int. Cl.⁴ ..................... A01N 25/00; A01N 35/00
[52] U.S. Cl. ........................................ 424/84; 514/675
[58] Field of Search ................... 424/331, 84; 514/675

[56] References Cited

U.S. PATENT DOCUMENTS

| 3,501,566 | 3/1970 | Burkholder et al. | 424/84 |
| 3,895,078 | 7/1975 | Gueldner et al. | 424/84 |
| 3,954,968 | 5/1976 | McKibben | 424/84 |
| 4,034,080 | 7/1977 | Silverstein et al. | 424/84 |
| 4,170,631 | 10/1979 | Young et al. | 424/84 |
| 4,179,446 | 12/1979 | Tumlinson, III et al. | 424/84 |
| 4,317,836 | 3/1982 | Chuman et al. | 424/84 |

OTHER PUBLICATIONS

P. L. Guss et al., "Identification of a Female-Produced Sex Pheromone of the Western Corn Rootworm," J. Chem. Ecol. 8(2):545–556 (1982).

T. F. Branson et al., "Winter Populations of Some Diabrotica[1] in Central Mexico: Voltinism and Pheromone Response," Ann. Entomol. Soc. Amer., 71(2):165–166 (Mar. 1978).

P. E. Sonnet, "Syntheses of the Stereoisomers of the Sex Pheromones of the Southern Corn Rootworm and Lesser Tea Tortrix," J. Org. Chem., 47(19):3793–3796 (1982).

Primary Examiner—Allen J. Robinson
Assistant Examiner—John M. Kilcoyne
Attorney, Agent, or Firm—M. Howard Silverstein; David G. McConnell; Curtis P. Ribando

[57] ABSTRACT

A pheromonal compound produced by the southern corn rootworm has been identified as 10-methyl-2-tridecanone (10-M-2-T) having the structural formula:

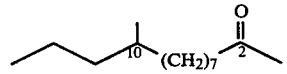

The synthetic R-enantiomer of 10-M-2-T demonstrates activity toward the southern corn rootworm comparable to its natural counterpart, whereas the synthetic racemic mixture is characterized by approximately half the activity for a given amount. Related diabroticites such as the western spotted cucumber beetle also respond to the synthetic compounds. By attracting adult beetles to field traps, 10-M-2-T is a useful tool for the monitoring and control of these major agricultural pests.

4 Claims, No Drawings

SYNTHETIC PHEROMONE 10-METHYL-2-TRIDECANONE AND ITS USE IN CONTROLLING THE SOUTHERN CORN ROOTWORM AND RELATED DIABROTICITES

This is a division of application Ser. No. 06/461,299, filed on Jan. 27, 1983, now U.S. Pat. No. 4,474,991.

BACKGROUND OF THE INVENTION

1. Field of the Invention

The genus Diabrotica comprises many of the economically important field pests afflicting U.S. agriculture. In the adult stage the diabroticites are responsible for damage to a variety of fruits and fruit trees. They also feed on the leaves of cucumber and other vine crops including peanuts, the squashes (Curcubita) and melons (Cucumis and Citrullas). The larvae of several species are notorious for their damage to corn crops. The northern corn rootworm (NCR), *D. longicornis barberi* Smith and Lawrence, for instance, is an important corn pest in the upper Mississippi Valley region. The western corn rootworm (WCR), *D. virgifera virgifera* LeConte, and the Mexican corn rootworm (MCR). *D. virgifera zeae* Krysan and Smith, are significant pests in the midwestern and southcentral regions of the United States, respectively.

Another group of diabroticites associated with extensive feeding damage and implicated as vectors of a number of plant diseases is *D. undecimpunctata*. The southern corn rootworm (SCR), *D. u. howardi* Barber, commonly known in the adult stage as the spotted cucumber beetle, ranges east of the Rockies from southern Canada into Mexico. Larvae of the SCR are most damaging to corn in the southeastern U.S. where those hatched from eggs of overwintering adults either feed on seedling corn roots or bore into the base of the stem. They also cause widespread damage to peanut crops by penetrating the developing peanut, either consuming it or providing entry for pathogenic microorganisms. The larvae attack most other legumes and are also a significant pest of the cucurbits. Adults have been collected from some 280 species of plants, but are of primary concern on cucurbits and peanuts. The western spotted cucumber beetle (WSCB), *D. u. undecimpunctata* Mannerheim is found in the far western United States and the upper Baja Peninsula. In the Pacific Northwest, it has been known to cause severe damage to forage crops. Another diaborticite closely related to the SCR and the WSCB is *D. u. duodecimnotata* Harold indigenous to Mexico.

The continued search for alternatives to the widespread application of insecticides has led to the investigation of sex attractants as potential agents for use in integrated pest management. A number of economically important insects are currently monitored, partially controlled, or completely controlled by use of their own specific sex pheromone. In the case of Diabrotica, application of this technology awaits identification and availability of the pheromones.

2. Description of the Prior Art

The production of a natural sex attractant by a species of Diabrotica was recognized by Cuthbert, Jr., et al. [J. Econ. Entomol. 57: 247–250 (1964)]. Female abdomen alcohol extracts (10 female equivalents) of the banded cucumber beetle, *D. balteata* LeConte, were reported to lure males of this species from distances as far as 49 ft. (15 m.).

In an unpublished Ph.D. thesis [University of Nebraska, Lincoln (1968)], Cates was able to show that for the WCR a mating or copulation stimulant was produced by 6-day-old virgin females, but he could not conclusively demonstrate the presence of a sex attractant. Subsequently, Ball et al. [J. Econ. Entomol. 66: 1051–1053 (1973)] reported that hexane extracts from field-collected WCR females were attractive to WCR males under field conditions. Guss et al. [J. Chem. Ecol. 8: 545–555 (1982) and U.S. patent application Ser. No. 408,569] succeeded in both identifying and synthesizing the WCR sex pheromone. The active compound, 8-methyl-2-decanol propanoate (8-M-2-DP) has proven to be an effective attractant for adult males of the WCR, NCR, and the MCR, but it does not elicit a response from the SCR. However, a report by Branson et al. [Ann. Entomol. Soc. Amer. 71: 165–166 (1978)] that males of *D. u. duodecimnotata* in Mexico are attracted to traps baited with unfractionated volatiles from female SCR originating in South Dakota suggests the existence of a pheromone specific to the *D. u. species*.

SUMMARY OF THE INVENTION

We have now for the first time obtained in pure or substantially pure form the major female-produced sex pheromone of the SCR. This compound, identified as 10-methyl-2-tridecanone (10-M-2-T) has been isolated from virgin females of the SCR and has also been successfully synthesized. It is an effective attractant for SCR males as well as the males of at least the related subspecies, *D. u. undecimpunctata* and *D. u. duodecimnotata*. Its usefulness in eliciting a behavioral response when applied to a locus of such males suggests two primary economic applications: (1) the monitoring of existing adult populations in order to predict infestation levels the following year for scheduling of treatment with larval insecticides; and (2) the control of reproduction in adult populations either by direct disruption of mating through confusing or inhibitory properties, or by attracting a demographically significant portion of the male population for subsequent destruction or sterilization.

In accordance with this discovery it is an object of the invention to identify a unique sex pheromone from a representative of the family Chrysomelidae, and more particularly from the genus Diabrotica.

It is also an object of the invention to produce racemic 10-M-2-T as the synthetic counterpart of the natural SCR sex pheromone.

A further object of the invention is to utilize 10-M-2-T as a monitoring or control agent for economically important species of corn rootworms.

Other objects and advantages of this invention will become readily apparent from the ensuing description.

DETAILED DESCRIPTION OF THE INVENTION

The isolation and identification of the sex pheromone from SCR females is described in detail on Example 1, below. The male response to 10-M-2-T of other *D. undecimpunctata* subspecies including the WSCB and *D. u. duodecimnotata* suggest that its biosynthesis is not limited to the SCR.

The 10-M-2-T compound of this invention is characterized by the following structural formula:

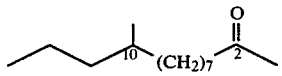

It is apparent therefrom that the compound may exist as either of two stereochemical configurations by virtue of chiral carbon 10. Present bioassay data indicate that the natural pheromonal compound isolated from the SCR is exclusively the R-enantiomer. This is also the isomer characterized by the highest activity toward males of the taxa. The scarcity of the natural isolate coupled with the inherent difficulty and economic disincentive of producing pure R-enantiomer by directed sterochemical synthesis tends to favor the synthetic racemic 10-M-2-T for commercial utilization. The racemic compound is approximated half as active toward the aforementioned rootworms as the natural pheromone when placed in field traps in microgram quantities. This suggests that the S-enantiomer does not inhibit the activity of the R form and functions in effect as a diluent.

As previously discussed, the synthetic pheromone may be used as either a monitoring agent or a control agent for adult beetles. In practice, the 10-M-2-T is used as a trap bait or is otherwise applied to a locus of the adults in an amount effective to induce the desired male response. In the case of an attractant response, for example, an effective amount is defined as that quantity of agent which attracts $D. u.$ males to the location of a bait at a rate significantly higher than males are attracted to a nonbaited location. Under typical field conditions, amounts in excess of about 0.5 $\mu$g. will be effective. Factors such as population density, temperature, wind velocity, and release rate will influence the actual number of beetles trapped.

It is envisioned that the 10-M-2-T would be effective in monitoring or controlling rootworm populations when used in conjunction with any type of trap or pheromone disseminator as known in the art. Typically, the compound would be applied to the device in solution with hexane or other suitable carrier. Volatilization can be retarded by inclusion of an oleaginous extender such as trioctanoin in an amount that is approximately 10% of the 10-M-2-T solution. Slow release may also be effected by encapsulation or absorption into a porous substrate.

The following examples are intended only to further illustrate the invention and are not intended to limit the scope of the invention which is defined by the claims.

EXAMPLE 1

Isolation of Natural Pheromone

For collection of pheromone, about 15,000 virgin SCR females 3–4 days postemergence were placed in a pheromone collection chamber comprising a metal screened cage (29×29×89 cm. o.d.) enclosed in a plexiglass box (31×31×91 cm. i.d.) containing a hole (35 mm. diameter) on either end. A glass tube (130×18 mm. i.d.) filled with about 15 g. "Porapak Q" for pheromone absorption was attached to one end of the plexiglass box with a rubber stopper and connected to a vacuum source. Air at a rate of 6.5 l./min. was passed over the insects and through the "Proapak Q" filter. The insects were provided with water and a dry diet mixed with a small amount of honey. Twice each week the apparatus was disassembled, and dead insects were removed and replaced with fresh females, and the food and water were changed. Once each week the "Porapak Q" filter was removed and replaced by a fresh one. At this time the live insects were transferred to a clean inner screened cage, and the plexiglass box was thoroughly cleaned before reassembly.

Pheromone was extracted from each filter with 50 ml. ether:hexane (60:40) in a 125-ml. Erlenmeyer flask. The mixture was allowed to steep with occasional agitation for 24 hr. after which the filter material was removed by filtration. The remaining solvent containing the pheromone was reduced in volume under vacuum at 0° C. to about 1 ml., and the concentrated solution was subjected to gas-liquid chromatography (GLC) without further treatment.

The ensuing fractionation was guided by laboratory bioassay techniques developed for the western corn rootworm (Guss et al. publication, supra).

Four or five male SCR beetles were placed in a disposable petri dish (150×15 mm.) and allowed to become acclimated for 15 min. Then a test compound in 1–5 $\mu$l. hexane was applied to a filter paper chip (5 mm.$^2$), and after solvent evaporation (about 10 min.), the treated chip was placed in the petri dish. Positive responses consisted of orientation of the beetles toward the chip, distinctive antennal waving, and copulatory behavior toward the other males.

Micropreparative GLC for isolation of the pheromone was performed on a "Varian Model 1400" gas chromatograph equipped with a flame ionization detector. Stainless steel columns were packed with 30% diethylene glycol succinate (DEGS) on 60/80 mesh "Chromosorb-W" (2 mm. i.d.×9.1 m.) and 1.5% "OV-101" on 100/120 mesh "Chromosorb G-HP" (2 mm. i.d.×1.5 m.). The injection port temperatures were 185° C. and 160° C. with each column type, respectively; the detector temperature was 250° C. The DEGS and the "OV-101" columns were maintained at 165° C. and 130° C., respectively. The carrier gas (N$_2$) flow rate through all columns was 20 ml./min. The chromatograph was modified to accomodate a 90:10 effluent splitter and an external dry-ice-cooled fraction collector. Fractions were collected in 1.5 mm.×305 mm. capillary tubes and were subsequently eluted with a minimal volume of hexane.

Upon fractionation of the "Porapak" collected volatiles on the DEGS, activity was confined to a single area of the chromatogram eluting after 42–46 min. Subsequent refractionation of this active area on the "OV-101" also produced a single, well-resolved peak of activity eluting after 20–24 min. Comparison of the active peak of each chromatogram with paraffin hydrocarbons yielded a retention index of 2020 on DEGS and 1540 on "OV-101." Analysis of the purified pheromone from the packed "OV-101" column on "OV-101" and "SP 2340" capillary columns indicated that it was about 99% pure. Approximately 60 $\mu$g. of pure pheromone was obtained from about 50,000 virgin females over a 3-month period. Analysis by a combination of gas chromatography, mass spectroscopy, and NMR led to the identification of the pheromone as 10-methyl-2-tridecanone.

EXAMPLE 2

Synthesis of Racemic 10-M-2-T

The synthesis of racemic 10-methyl-2-tridecanone, I, as described in the reaction scheme below commenced with the reaction of methyl cyclopropyl ketone and N-propyl magnesium chloride. The intermediate tertiary carbinol was isomerized to the homoallylic bromide, II (b.p. 91°–93° C. at 27 mm., yield: 58%) using cold 48% hydrobromic acid. Compound II was reduced to 1-bromo-4-methylheptane, III, by hydrogenation with platinum oxide in propionic acid [91% crude yield; NMR (CDCl$_3$) 0.86 (t, C$\underline{H}_3$CH$_2$), 0.87 (d, CH$_3$C$\underline{H}$), 3.40 (m, 2H, CH$_2$C$\underline{H}_2$Br)]. Bromide III was converted first to a Grignard reagent and then to a cuprate with methyl copper. The organocuprate was coupled to the propionate ester of 6-iodo-2-hexanol, IV, to give the required carbon skeleton in the form of propionate ester V [IR (CCl$_4$) 1740 cm.$^{-1}$; CIMS: (M+1)$^+$271, (M+1—CO$_2$C$_2$H$_5$)$^+$197]. Saponification of V produced alcohol VI in 68% overall yield from III [IR (CCl$_4$) 3640 cm.$^{-1}$; NMR (CDCl$_3$) CIMS: (M)$^+$214, (M-1)$^+$213, (M+1-18)$^+$197]. Oxidation of VI to VII was accomplished with aqueous acidic dichromate in near quantitative yield [IR (CCl$_4$) 1720 cm.$^{-1}$; NMR (CDCl$_3$) 2.13 (s, 3H, C$\underline{H}_3$=O), 2.42 (t, 2H, J=7.4 Hz, CH$_2$C$\underline{H}_2$C=O), CIMS: (M+1)$^+$213].

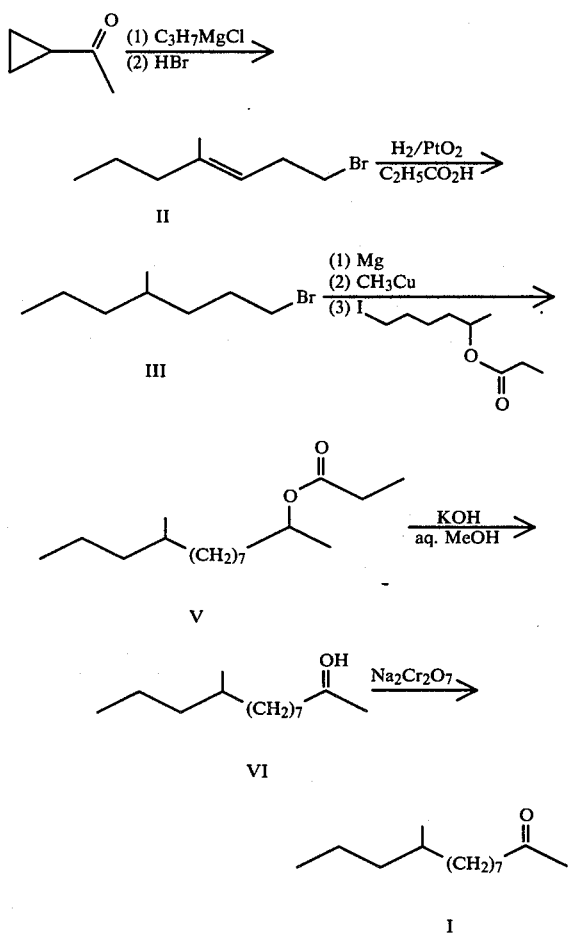

The synthesized 10-methyl-2-tridecanone was purified by high performance liquid chromatography (HPLC) on "Lichrosorb S160." GLC analysis of the material collected from HPLC on "SP 2340" and "OV-101" capillary columns indicated that it was greater than 99% pure. The pure natural pheromone prepared by the isolation procedure of Example 1 and the synthesized 10-methyl-2-tridecanone cochromatographed on both capillary columns. The electron impact and chemical ionization mass spectra of the synthesized compound were identical to the respective spectra of the natural pheromone.

EXAMPLE 3

The attractive properties toward the SCR of various preparations of natural and synthetic SCR pheromone were compared under field conditions in plots of mixed cucurbits (squash, melon, cucumber) in Gainesville, FL. Traps were devised by running wooden dowels (0.63 cm.) through the mounting holes of "Zoecon 1C" trap liners so that each trap consisted of a vertical white cardboard panel with stick-em on one side. When the dowel was implanted in the ground the top of the trap was just above the height of the vegetation. For each test the traps were placed in a randomized complete block and treatment positions were rerandomized each time traps were checked. Traps were about 3 m. apart in each block, and two replicate blocks were 30 to 45 m. apart. Pheromone was dissolved in hexane and appropriate quantities of each solution were pipetted onto a 4.5-cm.-diameter Whatman No. 1 filter paper disc just prior to baiting the traps. The filter paper bait was fastened just below the top edge of the sticky surface of the panel ca. 3:20 to 4:30 p.m. each day. The results of six replicates of this experiment are reported in Table I.

EXAMPLE 4

The procedure of Example 3 was repeated with the racemic 10-M-2-T and the natural, pure pheromone each applied at 1 μg. in 25 μl. of hexane on the filter paper. A hexane blank was included as a control. The test was run for 3 days with two randomized blocks. Due to high volatility of both the natural and synthetic pheromones, attraction to the traps lasted only about 20 min. after baiting.

TABLE I

| Example | Pheromone source | Amount[1] | Mean ± SE[2] SCR males/trap/replicate |
|---|---|---|---|
| 3A | unpurified volatiles | 1 μg. | 21.8 ± 1.5 a |
| 3B | unpurified volatiles | 3 μg. | 42.8 ± 5.1 b |
| 3C | natural pure pheromone | 1 μg. | 22.4 ± 2.0 a |
| 3D | racemic synthetic 10-M-2-T | 2 μg. | 29.0 ± 4.2 a |

[1]Amount of active material based on GLC analysis.
[2]SE = standard error of the mean; means followed by different letters differ significantly, Duncan's NMR, P ≧ 0.01. Randomized complete block (2) experiment (n = 6).

The results reported in Table II, below, establish that twice the dose of racemic material was required to obtain attraction equal to the insect-produced pheromone. This suggests that only one enantiomer of the synthetic mixture is the active component.

EXAMPLE 5

The R- and S-enantiomers of 10-M-2-T were prepared by the process of Sonnet [J. Org. Chem. 47(19): 3793–3796 (1982)], herein incorporated by reference. The undecenoic acid starting material was deprotonated with 2 equivalents of lithium diisopropylamide (LDA) in THF and then alkylated with n-propyl bromide. The resulting α-alkylated acid was converted to the corresponding acid halide with SOCl$_2$ and then reacted with the appropriate (S)- or (R)-α-methylbenzylamine to yield the corresponding amides. The separated diastereomeric α-methylbenzylamides (≧99.6%) were then labilized to hydrolysis by N-alkylation using the sequence (1) LDA and (2) ethylene oxide. The N- hydroxyethylated amides were then converted to the corresponding amino esters (as perchlorate salts) or the acids by complete hydrolysis, and thereafter reduced to the carbinols with $LiAlH_4$. The configurationally pure carbinols were then converted to bromides by using $PPh_3.Br_2$ and then reduced with $LiEt_3BH$. Thereafter the alkenes obtained from oxidative workups were purified by column chromatography, hydroxymercurated, and reduced with $NaBH_4$ to give the secondary alcohols. Oxiation of the alcohols yielded the configurationally pure tridecanone enantiomers.

EXAMPLE 6

The attractive properties toward the SCR of the R- and S-enantiomers of 10-M-2-T prepared in Example 5 were compared to one another and to racemic 10-M-2-T under field conditions in peanut plots in Gainesville, FL. Traps were devised as described in Example 3 except that the filter paper disc was replaced with a 5×4.5 mm. section cut from a porous rubber septum. After the septum was extracted for 1 hr. with methylene chloride, it was impegnated with 100 µg. of the test material in 25 µl. of hexane. The object of this dispenser design was to prolong the release of pheromone after evaporation of the solvent.

TABLE II

| Example | Pheromone source | Amount[1] | Mean ± $SE^2$ SCR males/trap/replicate |
|---|---|---|---|
| 4A | natural pure pheromone | 1 µg. | 22.0 ± 3.9 a |
| 4B | racemic synthetic 10-M-2-T | 1 µg. | 11.5 ± 1.8 b |
| 4C | hexane blank | 0 | 0 c |

[1]Amount of active material based on GLC analysis.
[2]SE = standard error of the mean; means followed by different letters differ significantly, Duncan's NMR, P ≧ 0.01. Randomized complete block (2)experiment (n = 6).

The test traps were placed in an randomized complete block, with one block in each of three widely separated peanut fields. The traps were inspected and rerandomized within blocks each day. The results as set forth in Table III below suggest that the activity resides exclusively in the R-enantiomer.

EXAMPLE 7

The procedure of Example 6 was repeated with racemic 10-M-2-T at various dose levels. The test was conducted over a 4-day period in three replicate blocks. The results are reported in Table IV, below. The relatively low response at all dose levels in comparison to the previously described field studies is most likely attributable to low population density. These data exhibit a high log linear relationship ($R^2=0.95$) over the range of doses from 1 to 100 µg. Such a relationship is characteristic of dose-response effects with sex attractants.

EXAMPLE 8

The attractive properties toward the western spotted cucumber beetle of the racemic 10-M-2-T were tested in a snap bean field near Corvallis, OR, using traps similar to those described in Example 3 above fitted with a "Hercon" laminated plastic dispenser. Six traps were baited with 0.17 mg./cm.$^2$, six with 1.6 mg./cm.$^2$, and six were set out as unbaited controls. The traps were checked priodically throughout the 21-day test period. On day 18, the field was treated with a carbaryl insecticide resulting in a lower count on day 21. The beetle counts given in Table V below represent the total number of beetles collected in the six traps since the previous trap check. A plausible explanation for the reduced count at the 1.6 mg./cm.$^2$ level is that the pheromone pervades the locus of the trap, overwhelming the beetle's impulse to pinpoint the source.

It is understood that the foregoing detailed description is given merely by way of illustration and that modification and variations may be made therein without departing from the spirit and scope of the invention.

TABLE III

| Example | Synthetic material | Mean ± $SE^1$ SCR males/trap/replicate |
|---|---|---|
| 6A | R-enantiomer (≦0.4% S) | 73.5 ± 19.6 a |
| 6B | S-enantiomer (≦0.1% R) | 7.0 ± 2.3 b |
| 6C | 1:1 R + S (50 µg. each) | 53.9 ± 17.8 c |
| 6D | racemic I | 51.9 ± 12.6 c |

[1]SE = standard error of the mean; means followed by different letters differ significantly, Duncan's NMR using 2-way analysis of variance, P ≧ 0.05. Randomized complete block (3) experiment (n = 9).

TABLE IV

| Dose (µg.) | Mean ± $SE^1$ SCR males/trap/replicate |
|---|---|
| 100 | 8.7 ± 2.6 |
| 30 | 5.1 ± 1.5 |
| 10 | 2.8 ± 0.9 |
| 3 | 1.3 ± 0.7 |
| 1 | 0.1 ± 0.03 |
| 0.3 | 0 ± 0 |
| hexane blank | 0.1 ± 0.7 |

[1]SE = standard error of the mean; means followed by different letters differ significantly. Randomized complete block (3) experiment (n = 12).

TABLE V

| | Treatment/WSCB males per 6 traps | | |
|---|---|---|---|
| Day | 0.17 mg./cm.$^2$ | 1.6 mg./cm.$^2$ | Unbaited check |
| 2 | 131 | 61 | 0 |
| 5 | 141 | 31 | 0 |
| 7 | 450 | 109 | 0 |
| 9 | 759 | 133 | 2 |
| 14 | 1,214 | 302 | 0 |
| 16 | 1,380 | 205 | 1 |
| 21 | 374 | 74 | 0 |
| TOTAL = | 4,449 | 915 | 3 |
| Beetles per trap per day = | 35.3 | 7.3 | 0.02 |

We claim:

1. A method of attracting a male *Diabrotica undecimpunctata* adult to a locus for the monitoring or control of reproduction in adult populations, comprising applying to said locus an effective amount of 10-methyl-2-tridecanone in combination with a suitable carrier.

2. A method as described in claim 1 wherein said *Diabrotica undecimpunctata* is a subspecies selected from the group consisting of *D. u. howardi*, *D. u. undecimpunctata*, and *D. u. duodecimnotata*.

3. A method as described in claim 1 wherein said 10-methyl-2-tridecanone is the racemic mixture of its R- and S-enantiomers.

4. A method as described in claim 1 wherein said 10-methyl-2-tridecanone is configurationally biased in favor of its R-enantiomer.

* * * * *